United States Patent
Cambronne et al.

(10) Patent No.: US 11,167,121 B2
(45) Date of Patent: *Nov. 9, 2021

(54) INTRAVASCULAR PUMP WITH INTEGRATED ISOLATED CONDUCTOR(S) AND METHODS THEREOF

(71) Applicant: Cardiovascular Systems, Inc., New Brighton, MN (US)

(72) Inventors: Matthew D. Cambronne, North Oaks, MN (US); Joseph P. Higgins, Minnetonka, MN (US); Matthew W. Tilstra, Rogers, MN (US); Benjamin D. Haselman, St. Paul, MN (US); Tristan A. Van de Moortele, Minneapolis, MN (US)

(73) Assignee: Cardiovascular Systems, Inc.

( * ) Notice: Subject to any disclaimer, the term of this patent is extended or adjusted under 35 U.S.C. 154(b) by 4 days.

This patent is subject to a terminal disclaimer.

(21) Appl. No.: 16/410,256

(22) Filed: May 13, 2019

(65) Prior Publication Data

US 2019/0351119 A1    Nov. 21, 2019

Related U.S. Application Data

(60) Provisional application No. 62/671,554, filed on May 15, 2018.

(51) Int. Cl.
*A61M 60/205* (2021.01)
*A61M 60/135* (2021.01)
(Continued)

(52) U.S. Cl.
CPC ........ *A61M 60/135* (2021.01); *A61M 60/148* (2021.01); *A61M 60/205* (2021.01); *A61M 60/50* (2021.01); *A61M 60/857* (2021.01)

(58) Field of Classification Search
CPC ...... A61M 1/125; A61M 1/122; A61M 1/101; A61M 1/1008; A61M 1/1086;
(Continued)

(56) References Cited

U.S. PATENT DOCUMENTS 5,662,699 A    9/1997  Hamedi et al.
6,007,478 A *  12/1999 Siess ................. A61M 25/0068
                                                        600/16

(Continued)

OTHER PUBLICATIONS

International Search Report and Written Opinion issued in PCT application No. PCT/US2019/32132, dated Aug. 8, 2019.
(Continued)

*Primary Examiner* — Lynsey C Eiseman
*Assistant Examiner* — Jessica L Mullins
(74) *Attorney, Agent, or Firm* — Barnes & Thornburg LLP; Jeffrey R. Stone

(57) ABSTRACT

The present invention provides an intravascular blood pump comprising a housing region that may be expandable, wherein the housing region comprises a series of troughs extending along at least a portion of the length of the housing region, wherein the integrated lead trough(s) may be defined by or within the housing region and wherein each adjacent pair of troughs are separated by an insulated spacing gap and may be covered to form insulated conduits. The integrated lead trough(s) may be configured to receive one or more electrical leads therein.

25 Claims, 4 Drawing Sheets

(51) Int. Cl.
*A61M 60/148* (2021.01)
*A61M 60/50* (2021.01)
*A61M 60/857* (2021.01)

(58) Field of Classification Search
CPC .... A61M 60/00; A61M 60/205; A61M 60/40; A61M 60/50; A61M 60/122; A61M 60/419
See application file for complete search history.

(56) References Cited

U.S. PATENT DOCUMENTS

| | | | |
|---|---|---|---|
| 7,011,620 B1* | 3/2006 | Siess | H02K 7/083 |
| | | | 600/16 |
| 2003/0199779 A1 | 10/2003 | Muhlenberg et al. | |
| 2005/0021015 A1 | 1/2005 | Keidar | |
| 2015/0141842 A1* | 5/2015 | Spanier | A61M 60/205 |
| | | | 600/478 |
| 2016/0136343 A1* | 5/2016 | Anagnostopoulos | |
| | | | A61M 60/562 |
| | | | 600/18 |
| 2017/0049947 A1* | 2/2017 | Corbett | A61M 1/1024 |
| 2018/0021494 A1* | 1/2018 | Muller | A61M 60/135 |
| | | | 604/35 |

OTHER PUBLICATIONS

Notification Concerning Transmittal of International Preliminary Report on Patentability and IPRP, issued in related PCT application No. PCT/US2019/32132, dated Nov. 26, 2020.

* cited by examiner

INTRAVASCULAR PUMP WITH INTEGRATED ISOLATED CONDUCTOR(S) AND METHODS THEREOF

CROSS-REFERENCE TO RELATED APPLICATIONS

This application claims priority to Provisional Patent Application No. 62/671,570, filed May 15, 2018 and titled INTRAVASCULAR BLOOD PUMP HOUSING WITH INTEGRATED LEAD TROUGH(S), the contents of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The invention relates to an intravascular blood pump with integrated isolated conductor(s).

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a stationary inducer, also known as a flow straightener; a rotational impeller; and a stationary diffuser and/or outflow structure; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the stationary inducer 6 before being urged forward by the rotating impeller 8. The blood flow may then be modified by a stationary diffuser and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; and 8,992,163.

Known LVAD devices will typically comprise an angled housing to accommodate the aortic arch, the angle or bend generally in the range of 135 degrees.

LVAD devices with integrated motors within the housing must be small enough to allow atraumatic intravascular translation and positioning within the heart. Though various means are known to collapse portions of the device while within the catheter or delivery sheath, including the housing and/or the impeller or parts thereof such as the blades, the size of the collapsed device may be limited by the integrated motor.

In addition, the known LVAD devices comprise a delivery configuration wherein the housing and/or impeller, e.g., the blades on the impeller, may be reduced in diameter and, when delivered distally from the delivery catheter or sheath, the collapsed elements are enabled to expand. These devices are limited in several respects. First, the collapsing and expanding comprises at least a portion of the housing that, is occupied by the impeller. Second, the inflow region of the housing, that is the region distal to the rotational impeller and the stationary inducer or flow straightener, comprises an area of opportunity to optimize blood flow through the cannula or housing. Known LVAD or VAD devices do not take advantage of this opportunity. Third, known LVAD or VAD devices comprise a stationary inducer or flow straightener encountered by blood upon entry into the pump which can contribute to, inter alia, thrombosis and/or hemolysis. Fourth, reducing crossing profile of the VAD or LVAD device is critical for reasons discussed herein, a design requirement made more difficult by the need to extend electric leads across or along the housing of the device, wherein the electrical leads may be used for, e.g., powering and/or communicating with a motor or sensor(s) or other operational powered element. In this connection, electric leads require profile reduction to keep the crossing profile as low as possible, as well as insulation and/or spacing between adjacent leads where such insulation and/or spacing is necessary or desired.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 1:
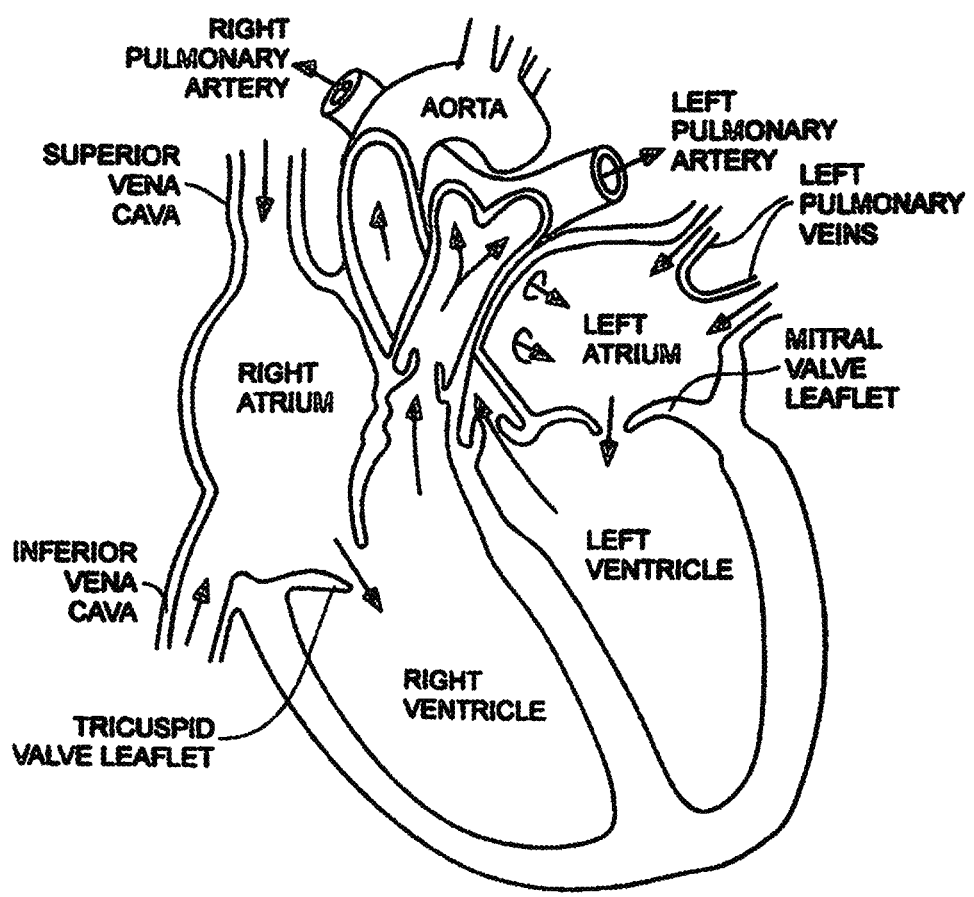
FIG. 1 is a cutaway view of the human heart.
Figure 2:
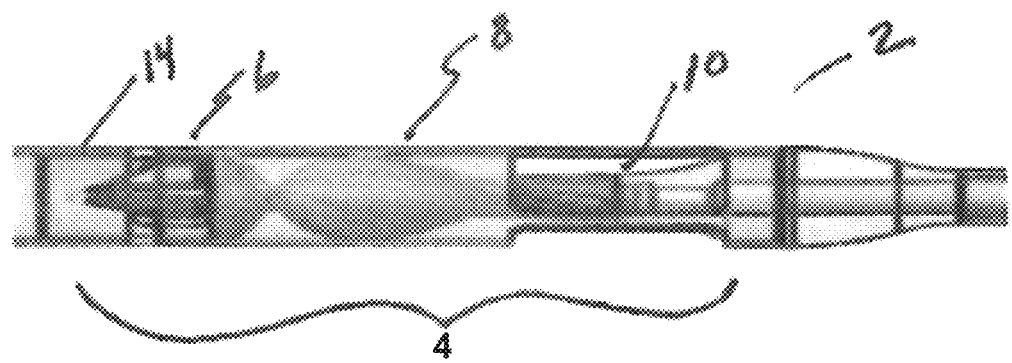
FIG. 2 is a cross-sectional view of a prior art device.
Figure 3:
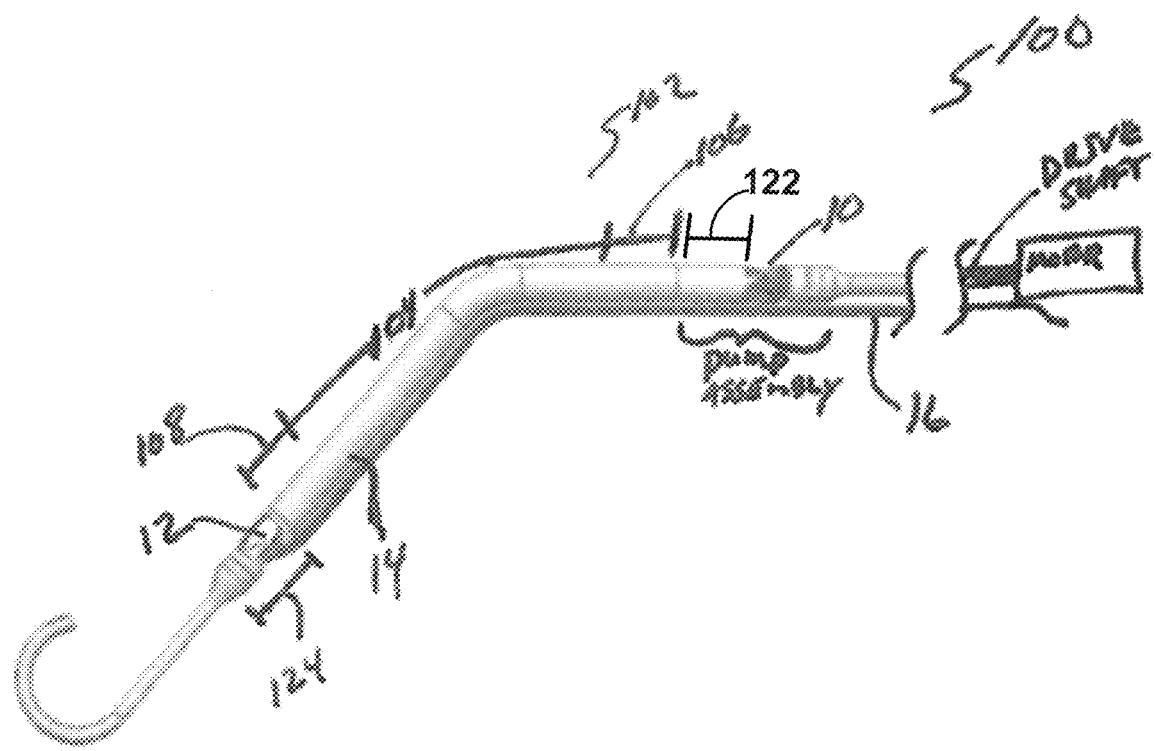
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller or rotor 8 or pump assembly. However, as is well known in the art, the motor may be located within the housing of the device itself, wherein the motor is typically mounted on the proximal side of the rotor 8 or impeller or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller or rotor 8 or pump assembly. The configuration shown in FIG. 3 may comprise a delivery configuration with an expandable region 102 compressed within an introducer or delivery sheath or catheter 200.

With reference generally to the Figures, the device 100 may comprise an expandable region 102 that may be located distal to the impeller or rotor or pump assembly, such that the housing diameter surrounding the impeller or rotor or pump assembly does not change diameter during delivery or during rotation. Stated differently, a proximal non-expandable region 122 may be provided and comprises at least the impeller or rotor or pump assembly and the housing surrounding that assembly does not expand or contract appreciably but may be flexible. Further, a distal non-expandable region 124 may also be provided comprising at least the inlet region including at least the inlet apertures 12. Thus, the expandable region 102 comprises a proximal end 106 and a distal end 108. The proximal end 106 of the expandable region 102 abuts or is adjacent to a distal end of the proximal non-expandable region 122 while the distal end 108 of the expandable region 102 abuts or is adjacent to a proximal end of the distal non-expandable region 124. The housing H surrounding the non-expandable region(s) 122, 124 may, however, be flexible or pliable, but they are not disposed to a biased expansion.

Alternatively, the housing H of device 100 in FIG. 3 may be non-expandable.

Figure 4:
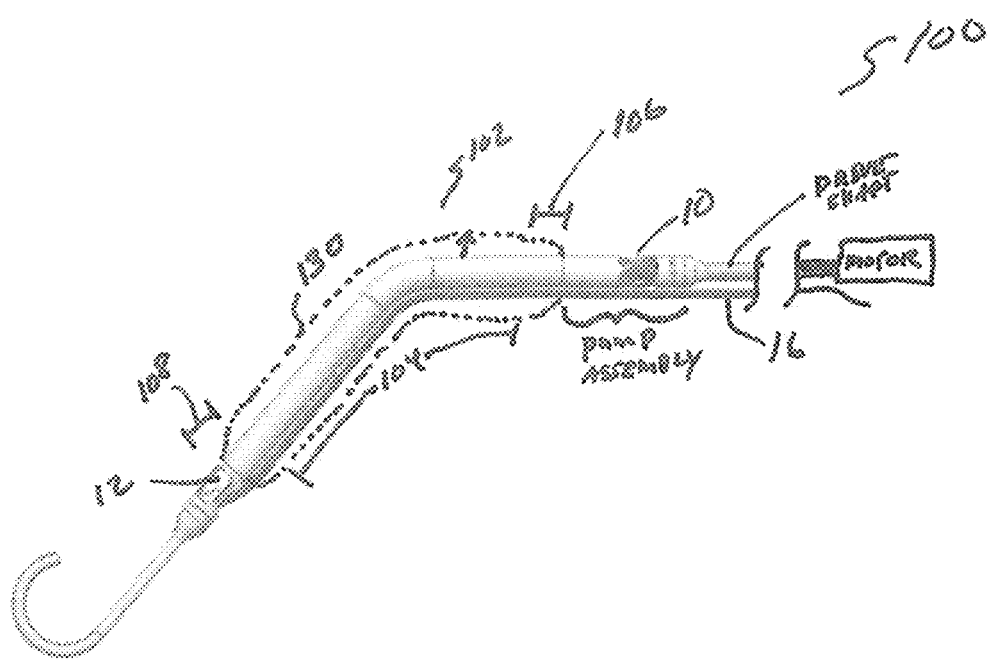
FIG. 4 is a side cutaway view of one embodiment of the present invention.

FIG. 4 illustrates an expandable embodiment of device 100 and in dashed lines the change in diameter to/from a collapsed, deformed expandable region to an exemplary expanded undeformed expandable region, extending distally from a point distal to the end of the impeller, rotor and/or pump assembly along the hollow cannula to a point just proximal of the inlet apertures. The expandable region 102 may expand to a maximum undeformed diameter within the range of 12-20 Fr, more preferably between 16-20 Fr. In contrast, the unexpanded region remains at a substantially fixed diameter within the range of 9 to 12 Fr.

With continued reference to FIGS. 3 and 4, and the remaining Figures generally, the device 100 may comprise an expandable region 102 that may be, either partially or completely, biased to the expanded configuration and, therefore, comprise a material or structure that facilitates expansion and may be biased to expand. Exemplary construction of the expandable region 102 may comprise a support structure 130 that is surrounded by an outer material, e.g., a jacket or coating or sleeve comprised of a plastic or polymeric material that accommodates an expansion of the underlying support structure as is known in the art. The support structure 130 may be formed of a shape memory material, for example Nitinol or similar. Other materials may comprise gold, tantalum, stainless steel, metal alloys, aerospace alloys and/or polymers including polymers that expand and contract upon exposure to relative heat and cold. In other cases, at least a portion of the expandable region 102, e.g., a central expandable section 104 discussed infra, may comprise a polymeric or other material sleeve that is configured to allow and/or accommodate expansion and collapsing and a support structure 130 may be omitted. FIG. 4 provides a rotational drive shaft connected with the impeller assembly and is, in turn, connected with a prime mover such as an electric motor that is located outside the patient's body. It will be understood, however, that the various embodiments of the inventions discussed herein may also be used in combination with blood pumps comprising motors integrated therein, i.e., no external motor. Further, as discussed above, device 100 may comprise an expandable housing H or region 102 or may be non-expandable.

In many of the embodiments described herein, the expandable region 102 may comprise a single expandable region, without need or reason to distinguish between a proximal transition section, central expandable section and/or distal transition section.

Generally, the expandable region 102 of the present invention may comprise a support structure 130 surrounded by a polymer coating or jacket that adapts to expansion and collapsing of the expandable region 102.

Further, the support structure 130 may comprise an expandable stent-like structure formed of a series of cells formed from interacting and/or interconnected wires and/or struts and that enable collapsing and biased expansion of a structure, e.g., a stent, as is known in the art. For example, see U.S. Pat. No. 5,776,183 to Kanesaka; U.S. Pat. No. 5,019,090 to Pinchuk; U.S. Pat. No. 5,161,547 to Tower; U.S. Pat. No. 4,950,227 to Savin; U.S. Pat. No. 5,314,472 to Fontaine; U.S. Pat. Nos. 4,886,062 and 4,969,458 to Wiktor; and U.S. Pat. No. 4,856,516 to Hillstead, the disclosures of each of which are hereby incorporated in their entirety by reference.

As illustrated in FIGS. 3 and 4, the expandable region 102 may comprise a single region capable of expansion and collapse.

The expandable region 102 described herein is merely exemplary and not limiting in any regard. As such, any expandable housing H of a blood pump device 100 is readily adaptable to the various embodiments of the present invention relating to insulation and/or spacing and/or profile reduction or integration of electrical leads or conductors E within or along the blood pump housing.

Alternatively, the housing H of the subject blood pump device 100 may not be expandable, embodiments that are also readily adaptable to the various embodiments of the present invention.

Turning now to FIGS. 5A, 5B a modified blood pump device 100' as describe supra is provided, with housing H that may be either expandable or non-expandable, and an exemplary layout of one or more lead troughs 300 integrated into, or defined by, or extending along, the expandable region and/or non-expandable housing H is illustrated.

Figure 5:
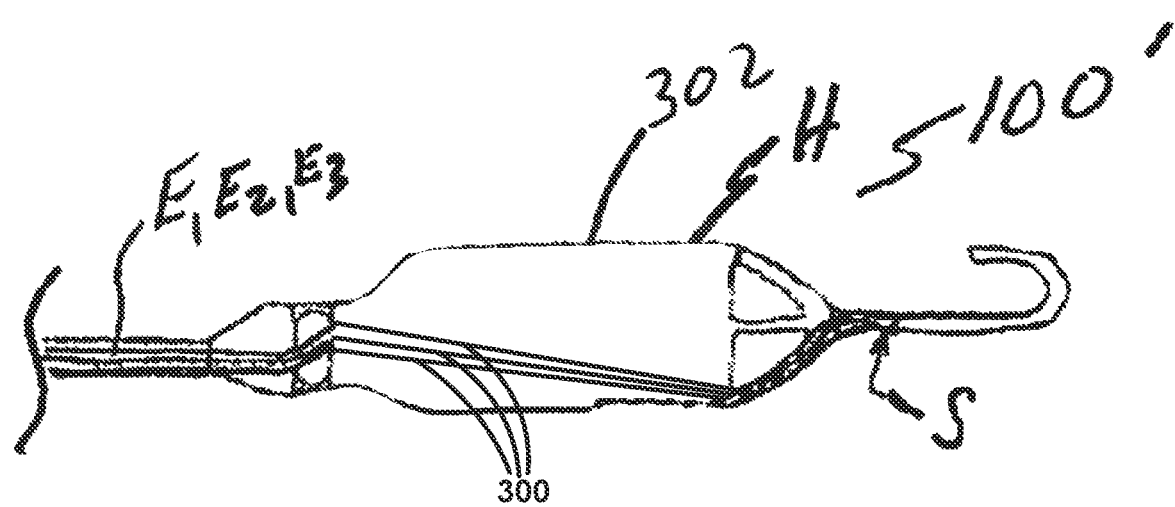
FIG. 5 is a side cutaway view of one embodiment of the present invention.

Thus, a lead trough 300 may be defined along the outer surface 302 of the housing H. Lead trough(s) 300 may run generally linearly from a distal point to a proximal point, in a generally axial direction as shown in FIG. 5, or may, as shown in FIG. 5A may comprise a spiraling shape around housing H, wherein the spiral or other configuration advances along housing H from, or between, a proximal point and a distal point. The depth and width and shaping of each lead trough 302 defined within the wall W of housing H may vary, but generally the width of the lead trough(s) 300 should allow at least one electrical lead to be disposed at least partially within the trough. Similarly, the depth may allow the at least one electrical lead or conductor E to be disposed at least partially within the lead trough 300. A preferred embodiment comprises the trough's depth and width of sufficient dimensions to allow the at least one electrical lead or conductor E to be fully disposed within the lead trough 300, with substantially no portion of the electrical lead or conductor E disposed therein rising above the outer surface 302 of the housing H. Further, the lead trough 300 may comprise a shaping that is at least partially complementary to the shaping of the at least one electrical lead or conductor E. Thus, a round lead trough 300 may be combined with at least one round electrical lead or conductor E disposed therein, or a square shaped lead trough 300 may be combined with at least one square shaped electrical lead or conductor E disposed therein.

FIG. 5A illustrates one embodiment of a blood pump device 100 comprising housing H that may, or may not be, expandable as discussed above. Housing H is defined, as best shown in FIG. 5B, by a wall W forming housing H, the pump assembly operationally disposed within housing H, also as described above. Three individual electrial leads $E_1$, $E_2$, $E_3$ arranged in spiraled groups, each individual lead disposed within one of the three lead troughs 300 spiraling around the housing H, defined in outer surface 302 of wall W forming housing H, wherein each electrical lead extends proximally through the lumen of the introducer sheath or catheter as shown. FIG. 5A further illustrates an exemplary sensor S operatively connected with one of the electrical leads $E_1$, $E_2$, $E_3$.

FIG. 5B is a cross-section of a portion of the expandable or non-expandable region of FIG. 5A showing the individual electrical leads $E_1$, $E_2$, $E_3$ and the grouping of the leads or conductors $E_1$, $E_2$, $E_3$ as they wind or spiral around the housing H. As shown the lead troughs 300 and associated leads $E_1$, $E_2$, $E_3$, each within a different lead trough 300 are coated or covered with a soft polymer 304 or other material. At this point, it will become clear that a conduit C is created for each individual electrical lead or conductor $E_1$, $E_2$, $E_3$. The lead troughs 300 may be uncovered in some embodiments or may be covered by a polymer jacket or, as shown in FIG. 5A may comprise a reflow or other polymer covering to create a conduit C.

There is an insulating separation between each electrical lead or conductor $E_1$, $E_2$, $E_3$, and a separation between adjacent groups of electrical leads or conductors, e.g., separation or spacing between adjacent leads $E_1$ and $E_3$ in each case. Three leads or conductors $E_1$, $E_2$, $E_3$ is merely exemplary, the necessary structure requires an insulating material M and/or a spacing or separation gap G between each adjacent electrical lead or conductor in a lead trough 300 or conduit C. These insulating separations may be achieved by simply spacing the electrical leads or conductors $E_1$, $E_2$, $E_3$ and/or groups of electrical lead or conductors away from each other. In other embodiments, the separations may be provided by interposition of insulating material, e.g., polymer, between all adjacent electrical leads or conductors, e.g., $E_1$, $E_2$, $E_3$. These interposing material embodiments may be formed by defining individual spaced-apart lead troughs 300 in the outer surface 302 of the housing H, wherein the electrical leads or conductors $E_1$, $E_2$, $E_3$ disposed within each lead trough 300 are held in place within a conduit C by an overlay material, a reflowed polymer material or the equivalent, or by a coating of insulating material such as a polymer or a polymer jacket.

In still other embodiments, the insulating separation or spacing between all individual adjacent leads $E_1$, $E_2$, $E_3$ may be achieved by melting the leads $E_1$, $E_2$, $E_3$ downward through the outer surface 302 of the housing H and into the wall W. In other embodiments, the insulating separation may be achieved by a process known as catheter printing, wherein the housing H is manufactured with the electrical lead(s) E formed and/or integrated with the housing H as a flex circuit or wherein at least a part of the housing H comprises a flexible circuit.

The arrangement of the two or more leads $E_1$, $E_2$, $E_3$ around or along the expandable region or non-expandable housing region H may be positioned or configured to enable a balanced expandable region or non-expandable housing region H in terms of relative mass located around and along the expandable region or non-expandable housing region H, but also in terms of current flowing along and around the expandable region or non-expandable housing region H.

The two or more electrical leads $E_1$, $E_2$, $E_3$ may further extend proximally through the lumen of the introducer sheath or catheter to a power supply, controller or other device. Thus, the working element(s) disposed along the at least one electrical lead $E_1$, $E_2$, $E_3$ may be controlled, may send or may receive signals sent along the at least one electrical lead and may be further displayed on a display that is in operative communication with the working element(s) and/or the controller.

The embodiment comprising a trough may comprise a single trough 300 or more than one trough 300. The one or more troughs 300 may also comprise a generally straight path from the proximal point to the distal point along the expandable region or non-expandable housing H or, alternatively, may comprise a non-linear path from the proximal point to the distal point along the expandable region or non-expandable housing H. For example, a spiral cut within the wall S around the expandable region or non-expandable housing H may be employed and as shown, wherein the spiral cut trench spirals around or circles the expandable region or non-expandable housing H moving from the proximal point to the distal point.

As seen in the Figures, once the at least one electrical lead $E_1$, $E_2$, $E_3$ is disposed within the at least one trough, physiological sensor(s) S or other working element(s) may be disposed therealong. For example and without limitation, flow rate sensors, pressure sensors, signal emitters, signal receptors and the like may be enabled by operative connection and communication with the at least one electrical lead. The working element(s) may be also disposed within an extension of the at least one trough 300 to reduce the collapsed crossing profile, as well as the expanded working profile, of the device with electrical lead(s) and working element(s). In certain embodiments, one working element may be disposed on an electrical lead in an upstream region relative to, e.g., the aortic valve, and a second working element may be disposed on an electrical lead in the downstream region relative to the aortic valve.

It is preferred that the device be configured as described above to move from a collapsed delivery configuration to an expanded working configuration, wherein the diameter of the expandable region and/or housing region will be larger in the expanded working configuration than the diameter of the collapsed delivery configuration. As a result, in some embodiments, the at least one electrical lead $E_1$, $E_2$, $E_3$ may be configured to slide along or within the associated trough 300 to accommodate the required added length of the at least one electrical lead moving from the collapsed to expanded configuration. Alternatively, sections of the at least one electrical lead 300 may be bunched or folded together in the collapsed configuration, wherein the additional length(s) of the electrical leads $E_1$, $E_2$, $E_3$ may be extended from bunched up or folded sections of lead to allow achieving the expanded configuration.

An alternate embodiment relating to the Figures comprises using the leads 300 as at least part of the expandable region's support structure. As shown in FIG. 5A, the support structure formed by the spiraling leads, and/or groups of leads, may comprise an inner coating and an outer coating, wherein the spiraling leads and/or groups of leads $E_1$, $E_2$, $E_3$ are configured to contract and expand and, in certain embodiments, may be biased to expand.

Still further, the leads and/or groups of leads $E_1$, $E_2$, $E_3$ may be configured as a portion of an expandable stent, wherein the stent is biased to expand and may be collapsed to the delivery profile. In these embodiments, the stent may be substantially manufactured from a self-expanding material such as, e.g., nitinol, with the leads forming a portion of the stent wherein, e.g., the leads may comprise a portion of interconnected stent cells. In this case, the portion of the stent formed by the leads may be, or may not be, biased to expand. The leads may be covered with an insulating material and may be separated from each other.

Moreover, in the case of a stent-like support structure configured to biasingly expand, the leads and/or groups of leads $E_1$, $E_2$, $E_3$ may be operatively attached to the interconnected stent cells, whereby expansion and collapsing of the stent-like support structure also results in radial movement of the attached leads and/or groups of leads.

In each of the above-referenced cases referring to stents or stent-like support structures, the expandable and/or self-expanding support structure comprises a stent-like structure that at least partially incorporates the leads and/or groups of leads in some fashion.

Finally, the leads and/or groups of leads $E_1$, $E_2$, $E_3$ may be arranged in any functional pattern within the expandable region.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump comprising:
an impeller assembly comprising a housing region defined by a wall forming an interior and having an outer surface, inlet apertures distal to the impeller assembly and outflow apertures proximal to the impeller assembly;
two or more troughs defined within the wall of the housing region and extending along the housing region from a distal point of the housing region to a proximal point of the housing region, the two or more troughs comprising a shape, a width, a depth and a length, wherein each of the two or more troughs do not extend into the interior of the housing;
wherein the length of the two or more troughs extends at least from the inlet apertures to the outflow apertures;
two or more electrical leads received and accommodated within respective ones of the two or more troughs, wherein the two or more electrical leads do not enter or extend into the interior of the housing,
wherein the shape, width and/or depth of the two or more troughs is selected such that each of the two or more electrical leads received within one of the two or more troughs does not extend outwardly beyond the outer surface of the housing; and an insulating material disposed between adjacent troughs of the two or more troughs.

2. The blood pump of claim 1, wherein the insulating material comprises a polymer.

3. The blood pump of claim 1, wherein the housing region is expandable.

4. The blood pump of claim 1, wherein the housing region is not expandable.

5. The blood pump of claim 1, further comprising an outer layer of material covering each of the two or more troughs and the electrical lead received within each of the two or more troughs.

6. The blood pump of claim 5, wherein the outer layer of material comprises a polymer.

7. The blood pump of claim 1, wherein each of the two or more troughs defines a linear path within the wall of the housing region.

8. The blood pump of claim 1, wherein each of the two or more troughs defines an at least partially non-linear path within the wall of the housing region.

9. The blood pump of claim 8, wherein each of the two or more troughs defines a spiral path within the wall of the housing.

10. The blood pump of claim 1, wherein the electrical lead received within each trough of the two or more troughs is fully disposed within a trough, such that the electrical lead does not extend beyond the outer surface of the wall of the housing region.

11. The blood pump of claim 1, further comprising a sensor operatively connected with at least one of the electrical leads received within the two or more troughs.

12. The blood pump of claim 11, wherein the sensor is selected from the group consisting of: flow rate sensor, pressure sensor, signal emitter, and signal receptor.

13. The blood pump of claim 1, further comprising an insulating spacing gap between each adjacent trough of the two or more troughs.

14. A blood pump comprising:
an impeller assembly comprising a housing region defined by a wall forming an interior and having an outer surface, inlet apertures distal to the impeller assembly and outflow apertures proximal to the impeller assembly;
two or more troughs defined within the wall of the housing region and extending along the housing region from a distal point of the housing region to a proximal point of the housing region, the two or more troughs comprising a shape, a width, a depth and a length,
wherein each of the two or more troughs do not extend into the interior of the housing;
wherein the length of the two or more troughs extends at least from the inlet apertures to the outflow apertures;
two or more electrical leads received and accommodated within respective ones of the two or more troughs, wherein the two or more electrical leads do not enter or extend into the interior of the housing;
wherein the shape, width and/or depth of the two or more troughs is selected such that each of the two or more electrical leads received within one of the two or more troughs does not extend outwardly beyond the outer surface of the housing; and
an insulating spacing gap disposed between adjacent troughs of the two or more troughs.

15. The blood pump of claim 14, wherein the housing region is expandable.

16. The blood pump of claim 14, wherein the housing region is not expandable.

17. The blood pump of claim 14, further comprising an outer layer of material covering each of the two or more troughs and the electrical lead received within each of the two or more troughs.

18. The blood pump of claim 17, wherein the outer layer of material comprises a polymer.

19. The blood pump of claim 14, wherein each of the two or more troughs defines a linear path within the wall of the housing region.

20. The blood pump of claim 14, wherein each of the two or more troughs defines an at least partially non-linear path within the wall of the housing region.

21. The blood pump of claim 14, wherein each of the two or more troughs defines a spiral path within the wall of the housing region.

22. The blood pump of claim 14, wherein the electrical lead received within each trough of the two or more troughs is fully disposed within a trough, wherein the electrical lead does not extend beyond the outer surface of the wall of the housing region.

23. The blood pump of claim 22, wherein the sensor is selected from the group consisting of: flow rate sensor, pressure sensor, signal emitter, and signal receptor.

24. The blood pump of claim 14, further comprising a sensor operatively connected with at least one of the electrical leads received within the two or more troughs.

25. The blood pump of claim 14, further comprising an insulating material disposed between adjacent troughs of the two or more troughs.

* * * * *